United States Patent [19]

Leffell et al.

[11] Patent Number: 4,894,547
[45] Date of Patent: Jan. 16, 1990

[54] OPTICAL METHOD AND APPARATUS FOR DETECTING AND MEASURING AGING, PHOTOAGING, DERMAL DISEASE AND PIGMENTATION IN SKIN

[75] Inventors: David J. Leffell, Ann Arbor, Mich.; Lawrence Deckelbaum, Woodbridge, Conn.

[73] Assignee: Yale University, New Haven, Conn.

[21] Appl. No.: 101,944

[22] Filed: Sep. 28, 1987

[51] Int. Cl.[4] .................. G01N 33/16; A61B 5/00
[52] U.S. Cl. .................. 250/461.2; 250/461.1; 250/459.1; 128/633
[58] Field of Search ............ 250/461.2, 461.1, 458.1, 250/459.1; 128/633, 634

[56] References Cited

U.S. PATENT DOCUMENTS

| | | | |
|---|---|---|---|
| 3,883,247 | 5/1975 | Adams | 250/461.2 |
| 3,992,631 | 11/1976 | Harte | 250/461.2 |
| 4,071,020 | 1/1978 | Pugliese | 250/461.2 |
| 4,178,917 | 12/1979 | Shapiro | 128/633 |
| 4,449,535 | 5/1984 | Renault | 128/634 |
| 4,564,598 | 1/1986 | Briggs | 250/461.2 |
| 4,577,109 | 3/1986 | Hirschfeld | 250/461.1 |
| 4,608,990 | 9/1986 | Elings | 128/633 |
| 4,675,529 | 6/1987 | Kushida | 250/458.1 |
| 4,753,530 | 6/1988 | Knight et al. | 356/318 |

Primary Examiner—Janice A. Howell
Assistant Examiner—William F. Rauchholz
Attorney, Agent, or Firm—Darby & Darby

[57] ABSTRACT

A method and apparatus for inducing fluorescence in human skin, in vivo, and for evaluating certain skin characteristics from the spectral intensity of induced fluorescence. The energy of a helium-cadmium laser is directed to a skin area to be evaluated by a fiberoptic element. The induced fluorescent energy having a wavelength band of interest above that of the laser wavelength, is directed to a device by a fiberoptic path for performing a spectral analysis of the fluorescent intensity. A ratio of chracteristic portions of fluorescent intensity of the skin area under test is developed and used to compare with different test subjects. The developed ratio, when taken in relation to the skin of subjects of different ages, indicates a marked difference in older subjects in comparison to that of very young subjects which correlates with long-term exposure of the skin to ultraviolet radiation. The method and apparatus are useful for evaluating skin pigmentation as well as for evaluating certain solid compounds such as amino acids.

29 Claims, 2 Drawing Sheets

OPTICAL METHOD AND APPARATUS FOR DETECTING AND MEASURING AGING, PHOTOAGING, DERMAL DISEASE AND PIGMENTATION IN SKIN

BACKGROUND OF THE INVENTION

1. Field of the Invention

The present invention relates to fluorescence of the human skin and, in particular, methods and apparatus for the inducement of production of skin fluorescence by ultraviolet energy and for evaluation of skin conditions as measured by skin fluorescence. The methods and apparatus of the invention also encompass inducement of fluorescence in specific chemical compounds which are not in solution, for the purposes of measurement and evaluation.

2. Description of the Prior Art

It is known that many compounds in animal and human tissue will fluoresce as a natural phenomenon. In vivo fluorescence of tissue after treatment with photo activatable compounds such as hematoporphyrins and tetracycline has been observed. There have been reports of fluorescence without benefit of exogenous dyes in the lens of diabetic patients and in dental caries. There are no known uses, however, of tissue fluorescence for in vivo diagnostic purposes. There are no known reports of whether induction of skin fluorescence, in vivo, can be of any diagnostic value.

The skin is the body's primary defense against the environment. It is continually exposed to ultraviolet radiation (UVR) from the sun which is known to hasten the aging process (of skin). The mechanism by which UVR ages skin is unknown, and, to a large extent, measurement of this effect has been limited to in vitro, qualitative, microscopic analysis. Testing for and measurement of skin aging has been limited to skin biopsies or the creation of plaster or rubber molds of the skin in conjunction with the surface scanning of the impression. Skin biopsies: (a) are invasive and traumatic; (b) are time-consuming; and (c) provide largely qualitative results. Plaster or rubber casts are difficult to use and also provide only qualitative results.

There has also been a need for the study of pigmented skin tissue by non-invasive methods. Known techniques, such as reflectance measurements, are not sufficiently sensitive for some purposes. More sensitive techniques are needed, for example, to study changes in pigmentation over a long period of time and would be particularly useful in the study of pigmented moles, especially as they relate to the subsequent development of melanoma skin cancer.

There has additionally been a need for the study of chemical compounds such as amino acids or polypeptides, without putting them in solution so as to avoid any concern about chemical alteration of the compounds during study and testing.

OBJECTS OF THE PRESENT INVENTION

An object of the present invention, therefore, is to provide a method and apparatus for inducing natural fluorescence of skin, in vivo.

Another object of the invention is to provide a method and apparatus for evaluating the spectra of fluorescence induced in skin, in vivo, in order to quantify changes in the integument that result from solar UVR exposure.

A further object of the invention is to provide a method and apparatus for measuring the aging of human skin which is non-invasive, rapid and provides quantitative results.

A still further object of the invention is to provide a method and apparatus for measuring skin pigmentation and changes in skin pigmentation, in vivo, by evaluating spectra of induced fluorescence.

Yet another object of the present invention is to provide a method and apparatus for evaluating chemical compounds in their natural powdered or solid form by induced fluorescence.

SUMMARY OF THE PRESENT INVENTION

The present invention encompasses apparatus for inducing fluorescence, in vivo, in human skin comprising means for producing light energy of a predetermined ultraviolet wavelength and of a predetermined power and means responsive to the light energy for directing the light energy to a skin area to be induced to fluorescence. In one form of the invention, the ultraviolet light energy producing means has a wavelength below that of the wavelength range of the induced fluorescence. In a preferred form of the invention, the ultraviolet light energy producing means is a laser and, in particular, a helium-cadmium laser which emits radiation at approximately 325 nm. A preferred form of the light energy directing means is a fiberoptic element.

The present invention also encompasses apparatus for measuring and quantifying induced fluorescence in human skin comprising means for sensing induced fluorescent radiation of human skin in vivo, means for performing a spectral analysis of the fluorescent radiation and means responsive to the sensing means for directing the sensed fluorescent radiation to the spectral analysis means. A preferred form of this apparatus employs a fiberoptic probe as the means for directing the sensed fluorescent radiation. A preferred form of apparatus for performing spectral analysis includes a spectrograph for spectral dispersion and an optical multichannel analyzer including a linear diode array coupled to a microchannel plate intensifier.

Further in accordance with the present invention, a method for inducing fluorescence in human skin, in vivo, comprises the steps of developing light energy of a predetermined ultraviolet band wavelength and directing the light energy to an area of skin to be induced to fluorescence. In a preferred form of the method, the light energy is developed by a laser and the method includes directing the ultraviolet light energy to the skin by a fiberoptic path.

In accordance with the present invention, furthermore, a method for quantifying and evaluating induced fluorescence comprises the steps of inducing a subject area to fluorescence, sensing the induced fluorescent radiation, obtaining a measure of intensity of said induced fluorescent radiation over a predetermined frequency band and using the measure of intensity as a basis to make comparisons between different test subject areas. A preferred form of the method includes forming a ratio of the measured fluorescent intensity of skin at two preselected wavelengths and, further, employing the ratio to determine the degree of long term exposure of the skin to solar ultraviolet radiation. The method, in one form of the invention, encompasses evaluating changes in skin pigmentation over a period of time by the measure of intensity of fluorescent radiation. In another form of the method of the invention, the subject area includes a particular compound to be tested, where the compound is of powdered or solid form.

For a better understanding of the present invention, reference is made to the following description and accompanying drawings, while the scope of the present invention will be pointed out in the appended claims.

DESCRIPTION OF THE PREFERRED EMBODIMENTS

The present invention employs laser-induced fluorescence of preselected subject areas. While a primary use of this technique relates to induced fluorescence of human skin, in vivo, the technique also has application to induced fluorescence of powdered or solid compounds, such as amino acids. With respect to these subject areas, the fluorescence is the result of exposing the subject area to ultraviolet radiation of a specific wavelength preferably using fiberoptic technology. The resultant fluorescence spectra have been found to have characteristic parameters which are useful in evaluating conditions of the subject areas.

When the radiation is applied to human skin, the resultant fluorescence has been found to be characteristic of exposed and sun-protected regions of the skin. Sun-exposed skin regions include, for example, the forehead, face and dorsal forearms of the subjects tested, while sun-protected regions typically involve skin in the buttocks region.

Figure 1:
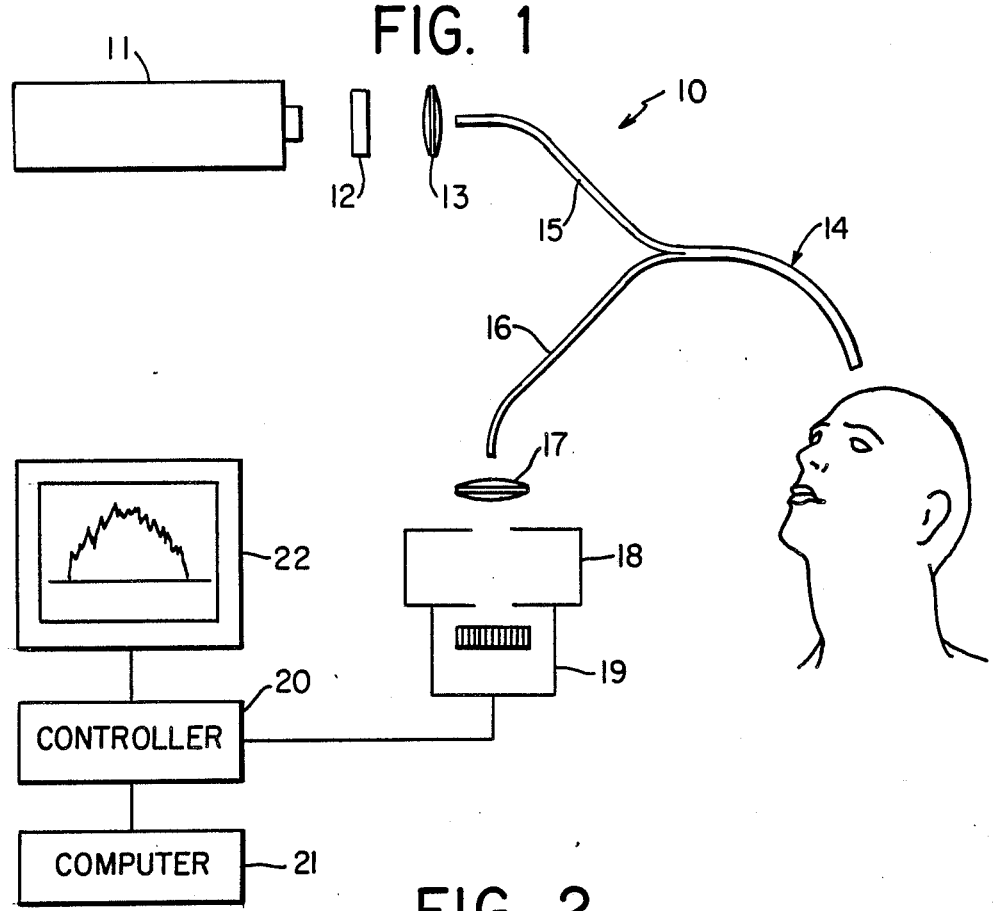
FIG. 1 represents in block form a system for inducing fluorescence, in vivo, in the human skin and for sensing and evaluating the induced radiation.

A preferred system used for inducing fluorescence in vivo in human skin and for evaluating the induced fluorescence is shown in FIG. 1. The system 10 incorporates a helium-cadmium laser, for example, Omnichrome model 356-5MS, emitting radiation at 325 nm at 1–10 mW continuous wave power. This radiation is applied in pulse form for a duration of approximately 300 ms. The laser output is coupled to the central fiber 15 of a coaxial fiberoptic probe 14 (EOTec Corporation, West Haven, Conn.) typically through a UV transmitting filter 12 and a lens 13. The distal end of the probe is placed a predetermined distance from the skin surface at several skin sites. A preferred distance is approximately 3 millimeters. Sun-protected sites include the buttocks and axillae. Sun-exposed areas include the shoulders, temple, forehead, and dorsa of the hands and forearms. These different locations represent variation in epidermal, dermal and subcutaneous thickness.

The human skin tissue induced to fluorescence, transmits its radiation by way of the coaxial fiberoptic probe through the fiberoptic bundle 16. The fluorescent energy emerges from the fiberoptic bundle and is focused by achromatic lens 17 onto a spectrograph 18. The spectrograph disperses the energy spectrally and images it onto an optical multichannel analyzer (for example, OMA Princeton Instruments, Inc., Princeton, N.J.) 19. The analyzer 19 consists of a linear diode array detector of 1,024 discrete elements coupled to a microchannel plate intensifier. The detector simultaneously detects the fluorescence intensity over a wavelength range of approximately 400 nm from 350 nm to 750 nm. The fluorescence spectrum is digitized using the diode array signals by controller 20 and the data stored and analyzed by computer 21, such as a IBM PC AT microcomputer. A CRT display 22 may be used for observing the spectral waveforms.

While much of the data has been collected with the distal end of the fiberoptic probe positioned 3 millimeters from the skin surface, other dimensions may be appropriate. Data has been collected with the location of the distal end positioned from contact (0 mm) to 3 mm from the skin surface. In the use of the laser, a pulse of laser energy with a duration of approximately 300 milliseconds has been found to induce fluorescence in the skin. If the applied pulse substantially less than this is employed, insufficient measurable fluorescence will be produced primarily because the signal-to-noise ratio is too small. A pulse duration up to 1–5 seconds may be used. Longer pulse widths may cause bleaching of the fluorescence signal. Pulse duration may also be achieved by a number of the 300 milliseconds individual pulses having shorter pulse widths (e.g. 3 pulses having 10 milliseconds pulse widths).

The wavelength of this laser is chosen to be below that of the spectral range of the induced fluorescence to insure that the measured response includes only that of the fluorescence and is not a reflection of applied laser energy. Since the developed fluorescence of skin is in the wavelength band of 350 to 750 nm, a laser having a wavelength below 350 is preferred. The helium-cadmium laser having a wavelength of 325 nm is a particularly preferred choice, however, other laser sources having a wavelength of up to 350 nm will also be effective. A non-laser ultraviolet light source having a band of wavelengths below 350 nm may also be used for the purposes defined above, if sufficient energy can be developed to induce fluorescence.

The power level of the laser within the 1 to 10 mW range is chosen so that the spectrograph and analyzer are not in saturation. Different power levels are required for different test subjects because the level of fluorescence will vary from subject to subject. By employing a ratio of a subject's sun-exposed skin to his (or her) own non-sun-exposed skin, the subject acts as his (or her) own control and the subject-to-subject level variations mentioned above are eliminated. It should be noted that power levels of 1 to 10 mW applied to human skin are totally harmless.

SPECIFIC TESTS AND RESULTS - PHOTO-INDUCED CHANGES IN SKIN

Three groups of subjects were studied using the above-described apparatus. Group 1 had a mean age of 3, Group 2 had a mean age of 30, while Group 3 had a mean age of 63. The resultant spectral waveform versus wavelength indicated a peak of fluorescence intensity at 390 nanometers, with a shoulder of the wave at 429 nanometers. A ratio of fluorescence intensity of these wavelengths was obtained and used to correlate the fluoresced skin with sun exposure. As discussed in more detail below, the solar-protected skin of Group 1 had a fluorescence intensity ratio of 1.19 while that of solar-exposed skin was 1.15. The sun protected skin of Groups 2 and 3 revealed intensity ratios similar to those of sun-protected skin of the youngest group (1.14 and 1.11). The solar-exposed skin of the older subjects, however, showed a significantly lower ratio (0.88 and 0.91). The conclusion was that fiberoptic fluorimetry, a non-invasive technique, allows for the quantitation of changes in the skin related to ultraviolet exposure. The choice of wavelengths of peak fluorescence activity for purposes of fluorescence intensity comparison is just one method of analysis of skin fluorescence in this system.

Tests were run on a group of 28 individuals categorized in Table 1 below.

TABLE 1

GROUPS OF SUBJECTS

| GROUP | N | AGE | SEX | SKIN TYPE | MEAN AGE |
|---|---|---|---|---|---|
| 1 | 7 | 1.3 | F | I | 2.96 +/−.06 |
|   |   | .5 | M | II |   |
|   |   | 4 | M | II |   |
|   |   | 4 | M | II |   |
|   |   | 3.3 | F | I |   |
|   |   | 3 | F | II |   |
|   |   | 3 | F | I |   |
| 2 | 13 | 28 | M | III | 29.6 +/− .83 |
|   |   | 24 | M | I |   |
|   |   | 27 | M | IV |   |
|   |   | 26 | M | II |   |
|   |   | 26 | M | II |   |
|   |   | 31 | M | II |   |
|   |   | 31 | M | II |   |
|   |   | 35 | M | I |   |
|   |   | 31 | M | I |   |
|   |   | 32 | M | II |   |
|   |   | 31 | M | I |   |
|   |   | 31 | F | II |   |
|   |   | 31 | M | II |   |
| 3 | 8 | 59 | M | I | 63 +/− 2.0 |
|   |   | 56 | M | I |   |
|   |   | 56 | M | II |   |
|   |   | 65 | M | I |   |
|   |   | 67 | M | I |   |
|   |   | 65 | M | III |   |
|   |   | 63 | M | I |   |
|   |   | 74 | M | II |   |

Group=the experimental group to which subjects were assigned based on age. N=number of subjects in each group. Age=years. Skin type: I=always burns; II=usually burns, occasionally tans; III=usually tans, may burn; IV=always tans. Mean age=years +/− standard error of the means.

Figure 2:
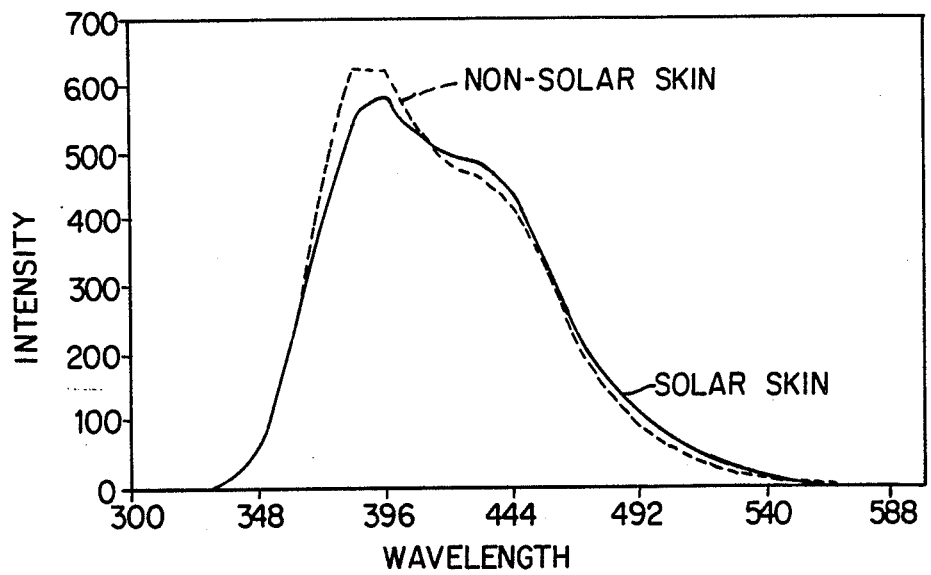
FIG. 2 represents a measured frequency spectrum using the method and apparatus of the present invention for a test sample of a three year old child taken from a body portion which has been exposed to the sun (solar skin) and a body portion which has not been so exposed (non-solar skin)
Figure 3:
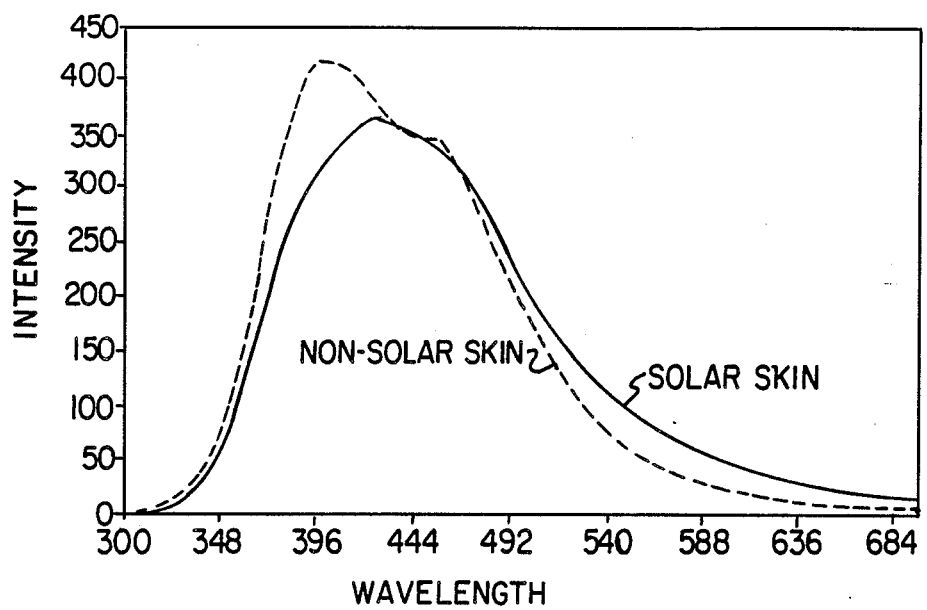
FIG. 3 represents a measured frequency spectrum using the method and apparatus of the present invention for a sample test of a 32 year old person taken from a body portion which has been exposed to the sun (solar skin) and a body portion which has not been exposed (non-solar skin)

In Group 1, the fluorescence pattern of sun-exposed skin did not vary significantly from that of sun-protected skin. FIG. 2 demonstrates the typical curve that was observed in this group of subjects with minimal environmental ultraviolet radiation exposure. The shoulder or second peak at 429 nm was characteristic of solar-protected skin in all groups but was present in solar-exposed skin in Group 1 only. In contrast to this, subjects in Group 2 showed a distinct difference in the fluorescence spectra between the sun-protected skin of the buttocks and axillae and the sun-exposed skin of the shoulders, forehead, and temple (FIG. 3). It should be noted that the graph of FIG. 2 actually represents the data for one 3 year old subject and the graph of FIG. 3 represents the data for one 32 year old subject. Both were chosen because they were typical of other members of their group.

To compare spectral patterns quantitatively, the ratio of the fluorescence intensity at 390 nm to 429 nm was calculated for each skin spectrum. This ratio (R 390/429) was chosen because relative fluorescence peaks were noted at these wavelengths in solar-protected skin but other methods of analysis and comparison are possible. (See Table II where P is defined as the Wilcoxon signed rank test comparing solar and non solar ratios in each group.)

In Group 1, there was no difference between sun-exposed and sun-protected skin in R(390/429) (Table II). In Group 2 R(390/429) of sun-protected skin was 1.14+/−0.04 and the ratio for sun-exposed skin was 0.88+/−0.02 (P<0.001). A similar difference between solar-exposed and solar-protected skin was found in Group 3 (1.11+/−0.04 versus 0.91+/−0.04; P<0.008). No significant difference between the R(390/429) value for sun-protected skin of Groups 1, 2 and 3 and the sun-exposed skin of Group 1 was noted. However, solar-exposed skin of Groups 2 and 3 differed significantly from all other groups (P<0.002 using the Kruskal-Wallis test).

TABLE II

| RATIOS OF FLUORESCENCE INTENSITY SOLAR-PROTECTED VERSUS SOLAR-EXPOSED SKIN | | | |
|---|---|---|---|
| GROUP | NON SOLAR | SOLAR | P |
| 1 | 1.19 +/− .06 | 1.15 +/− .06 | NS |
| 2 | 1.14 +/− .04 | .88 +/− .02 | .001 |
| 3 | 1.11 +/− .04 | .91 +/− .04 | .008 |

Solar refers to sun-exposed skin (forehead) and non-solar refers to sun-protected skin (buttocks). Values for buttocks were similar to those from axillae and values from the shoulders and upper back were similar to those of the forehead.

Ratios represent fluorescence intensity of subject's skin at wavelength 390 nm divided by the fluorescence intensity at wavelength 429 nm. Values=means +/− standard error of the mean.

P=Wilcoxon signed rank test comparing solar and non-solar ratios in each group.

Based on these and other similar data, the conclusion can be drawn that solar-exposed skin has a different inducible fluorescence pattern from solar-protected skin.

The similarity of spectra between solar-exposed and solar-protected skin in the youngest age group is consistent with the fact that these children have not yet had much sun exposure. Conversely, subjects in Groups 2 and 3 showed significant differences in the fluorescence of buttocks when compared with forehead or other solar-exposed areas. That the difference observed in Groups 2 and 3 were not simply a function of regional variation in skin thickness is confirmed by the fact that spectra of the buttocks were similar to those of the axillae—another sun-protected region of the body with different morphology. In addition, the fluorescence spectra of skin from the shoulders and upper back were similar to that of the forehead despite the consistently thicker dermal and subcutaneous tissue of the former sites.

In the process of measuring and analyzing induced fluorescence in human skin, in vivo, the source of the observed fluorescence has been considered.

In light microscopy, it is often the collagen and elastin that are thought to autofluoresce. Collagen, despite its slow turnover rate in adults, does change with age and perhaps with ultraviolet radiation exposure. However, the peak fluorescence of collagen in vitro did not correspond with the skin fluorescence patterns observed in the subjects tested above. Elastic tissue in skin and aorta changes with age and in the skin with exposure to ultraviolet radiation. The changes in elastic tissue in skin due to ultraviolet radiation are different from those due to chronologic age alone.

The changes in the fluorescence spectra induced and measured in accordance with the present invention appear to relate more to photo-induced changes than to aging itself. Since it is known that ultraviolet-induced changes in elastin are different from those due to age alone, components of elastic tissue may be responsible for the observed changes in the fluorescence pattern. One of the major cross-linking amino acids of elastin is desmosine. It has been demonstrated to increase four-fold in sun-exposed skin compared with sun-protected skin. In addition, it has been demonstrated that desmosine is a photo-reactive amino acid.

By the use of the apparatus of FIG. 1 on amino acids in solid form (i.e. powdered) or use of "crystalline", tests of induced fluorescene in various compounds were performed. The following peak intensities and wavelength of intensity were noted:

TABLE III

| COMPOUND | INTENSITY | WAVELENGTH |
|---|---|---|
| Desmosine | 3414 | 390 |
| Collagen | 2263 | 378 |
| Elastin | 2441 | 390 |
| Valine | 33 | 390 |
| Tryptophan | 1120 | 380 |
| Tyrosine | 546 | 367 |
| Proline | 30 | 423 |
| Lysine | 24 | 390 |
| Histidine | 102 | 388 |
| Glycine | 145 | 390 |
| Cystine | 70 | 414 |
| Aspartate | 248 | 391 |
| Arginine | 1381 | 390 |

Wavelength is in nanometers; intensity is in arbitrary units.

Figure 4:
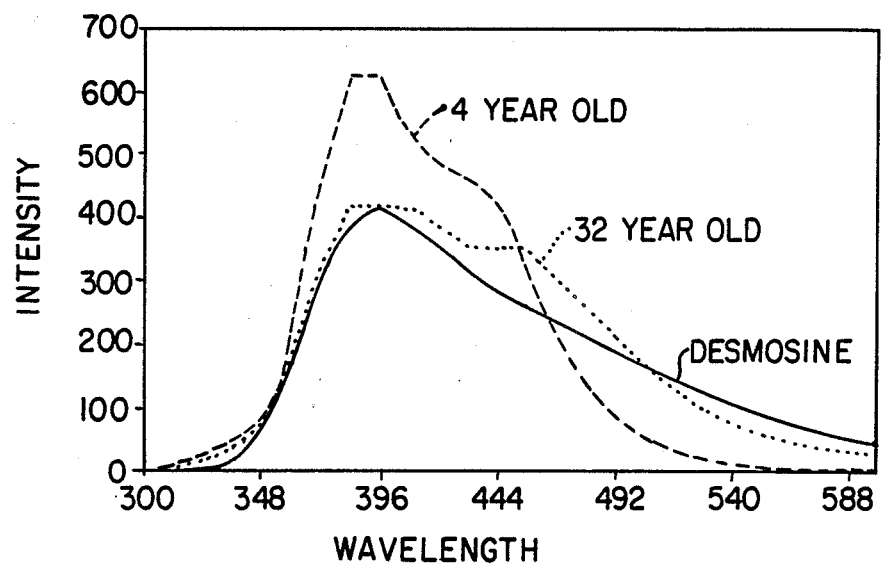
FIG. 4 is a graph of laser induced fluorescence of desmosine in comparison with non-solar skin of a 4 and 32 year old subject.

This data shows that fluorescence in skin is most likely from elastin, more specifically, the highly fluorescent desmosine. This is supported by the location of the desmosine peak fluorescence intensity at 390 nm to that of peak sun-protected skin fluorescence intensity. In FIG. 4, the spectrum of this amino acid is compared with that of sun-protected skin from two patients. The R (390/429) of desomisine was 1.24. The peak fluorescence of collagen occurred at 378 nm while that of elastin was at 390 nm.

The possibility that pigmentation may be significantly affecting the fluorescence spectra was addressed by analysis of patients with Type IV skin or darkly pigmented individuals. Absolute ratios for both solar and non-solar skin of this type were lower than the average for their group. The difference between sun-exposed and sun-protected sites in Groups 2 and 3 subjects, however, were significant by the paired-T-test. In addition, one individual was evaluated before and after natural tanning. A sun-protected patch on the forearm which did not tan was compared with the surrounding hyperpigmented skin. This skin site, all of the same chronological age, had not suffered chronic solar damage over the seven days of sun exposure. Spectral patterns from the tanned and non-sun-exposed solar forearms were statistically identical. This suggests that the unimodal pattern seen in solar skin is not necessarily a function of pigmentation that occurs in the epidermis, but most likely relates to the more chronic changes occurring deeper in the skin.

The inducement of fluorescence by the technology discussed above can also be used to sensitively measure pigmentation in the epidermis. By inducing fluorescence in the skin and measuring that which passes through the pigmented superficial layer of skin, one can detect variations in degree of pigmentation from site to site, or neighboring sites within a very close area. Because fluorescence represents biologic activity in the dermis, this technique will be useful for measuring epidermal pigmentation as well as the dermal pigmentation that is present in moles (nevi), some of which may become cancerous (melanoma).

An explanation of this occurrence is that once the helium-cadmium laser at 325 nm is directed to the skin, various compounds within the dermis become excited to fluorescence and that fluorescence passes back through the skin. However, the primary pigment of the skin, called melanin, is an excellent absorber or sink, for photons or light energy. As a result, the more pigmentation present, with a constant amount of fluorescence being induced, the less fluorescence will actually pass through the skin to be detected by the system already described.

In these experiments, the pigmentation in a particular strain of mice, called SKH, were evaluated. These mice are born with a pelt but lose it, as well as all their pigmentation by six months of age. Only their ears maintain their original color. These animals come in three shades: dark brown or black, tan, and white. The pigmented ears of each group were compared by measuring the fluorescence as described. The peak intensity occurred in most cases at 378 nm with another faint shoulder at 453 nm. A ratio of these two wavelengths was then chosen as a measure of transmitted fluorescence. The spectrum obtained was the same as previously described. The data is indicated in Table IV. Other methods of analysis of fluorescence of in vivo pigmentation exist other than the specific one described here.

TABLE IV

| RATIO | BROWN | TAN | ALBINO | |
|---|---|---|---|---|
| 378/453 nm | 3.64 | 3.06 | | p .001 |
| 378/453 | 3.64 | | 2.93 | p .001 |
| 378/453 | | 3.06 | 2.93 | p .4 (NS) |

Each mouse in each group were studied and a reading on each ear was performed (i.e. 8 readings in each group).

The above-described method and apparatus have immediate applications in a number of areas. An urgent need exists in the pharmaceutical industry for a means of testing new products thought to have an effect on the reversal of photoaging. Current technology involves the use of plaster casts of skin and the visual evaluation of surface photodamage (wrinkles). The quantitative method of measuring photoaging should prove valuable for this purpose, as well as for the evaluation of other products related to skin aging.

Preliminary evidence suggests that laser fluorimetry of the skin may be based on changes in the elastic tissue and collagen of the subcutaneous tissue. There are many skin diseases, some quite disabling, which involve alteration in the elastic tissue and/or collagen. This method may provide a means for early diagnosis as well as a means of following the success of therapy. These diseases include scleroderma, graft-vs.-host-disease, anetoderma, and abnormalities of the wound healing process. There are benign tumors of the skin that are composed of abnormal elastic tissue and collagen, and this method may be applicable as well for diagnostic purposes. Coupled with an ablative laser, therapeutic applications are possible.

In an appearance-conscious society, the method and apparatus of the present invention may have widespread appeal in a non-medical setting, specifically, the method may be used as a non-invasive one in commercial and cosmetic treatment centers which might be interested in laser fluorimetry to enhance their service to clients as part of their therapeutic regimen. Improvement in skin, relating to treatment, could be documented and recorded for the patient's benefit using the inventive method and system.

As discussed above, the inventive method and system may be used to study pigmented moles. As such, it may well be useful in evaluation of pre-malignant pigmented moles and may have widespread application for screening and treatment of pigmented moles.

Finally, the method and system of the present invention provide a valuable research tool for studying mechanisms of aging in a rapid, non-invasive fashion.

The apparatus for inducing and evaluating fluorescence is not restricted to the specifics of FIG. 1. Tests have been run where the fiberoptic bundle has been reduced to a single fiber. The helium-cadmium laser could be replaced by a diode laser emitting at a similar wavelength. A xenon lamp with a monochrometer could also be used as a simpler, less expensive light source. Instead of the optical multichannel analyzer, filters could be utilized that would transmit preferentially at the specific wavelength of interest (e.g. 390 and 429 nm). Photomultipliers could be used to record the intensity and an electronic circuit could calculate the pertinent ratios.

In present use, the surface area evaluated by the inventive system is about 1 mm. In cases where it is desirable to evaluate larger regions, the combination of laser-induced skin fluorescence with a digitizing system would allow for the evaluation of spectra from each of the many "pixels" comprising an area larger than 1 mm. Such an integrated system could then survey large areas of skin and produce a "map" of the skin with the relative degrees of aging pigmentation, or other factor coded in an easily visualized fashion. This would be valuable for pigmented lesions with variegated surfaces as well where a topographic map of variations in pigmentation could be created.

While the foregoing description and drawings represent the preferred embodiments of the present invention, it will be obvious to those skilled in the art that various changes and modifications may be made therein without departing from the true spirit and scope of the present invention.

What is claimed is:

1. Apparatus for inducing naturally occurring fluorescence, in vivo, in human skin and for measuring and quantifying such induced fluorescence for diagnostic purposes comprising:
    means for producing laser light energy having a predetermined wavelength and power;
    means responsive to said laser light energy for directing the laser light energy to an untreated skin area to induce endogenous fluorescence;
    means for receiving endogenous fluorescent radiation from the skin area induced to fluorescence by said laser light energy;
    means for performing a spectral analysis of said received fluorescent radiation and for developing a numerical value representative of a predetermined portion of said spectrum, said numerical value having use as a diagnostic measure of the untreated skin area induced to endogenous fluorescence; and
    means responsive to said receiving means for directing said received endogenous fluorescent radiation to said spectral analysis means.

2. The apparatus of claim 1, wherein said means for producing laser light energy is a helium-cadmium laser which emits radiation at approximately 325 nm.

3. The apparatus of claim 2, wherein said laser energy is applied at a power level of between 1 to 10 mW for a predetermined length of time.

4. The apparatus of claim 3, wherein said laser energy is applied for approximately 300 ms.

5. The apparatus for claim 1, wherein said means for directing said laser light energy is a fiberoptic element.

6. The apparatus of claim 5, wherein said fiberoptic element is a central fiber of a coaxial fiberoptic probe placed from 0 mm to approximately 3 mm from the skin surface.

7. The apparatus of claim 1, wherein said means for performing spectral analysis includes a spectrograph for spectral dispersion and an optical multichannel analyzer including a linear diode array coupled to a microchannel plate intensifier.

8. The apparatus of claim 7, wherein the spectral analysis means detects fluorescence over a wavelength range of approximately 400 nm.

9. The apparatus of claim 8, wherein said range is from 350 nm to 750 nm.

10. The apparatus of claim 7, including means for recording the frequency spectrum of the detected fluorescence and for calculating a numerical value representative of a predetermined portion of said spectrum.

11. The apparatus of claim 7, including means for displaying the frequency spectrum of the detected fluorescence.

12. A method for inducing naturally occurring fluorescence in untreated human skin, in vivo, comprising the steps of:
    developing laser light energy of a predetermined ultraviolet band wavelength; and
    directing said laser light energy to an area of untreated skin to be induced to endogenous fluorescence.

13. The method of claim 12, wherein said light energy is produced by a laser having a wavelength of approximately 325 nm.

14. The method of claim 13, wherein said laser energy has a power of from 1 to 10 mW and is applied for a predetermined length of time.

15. The method of claim 12, wherein said directing step includes directing said ultraviolet light energy to the skin area by a fiberoptic path.

16. The method of claim 15, wherein the fiberoptic path includes a distal end, the method including arranging the distal end to be adjacent the skin area to be exposed at a distance of from 0 mm to approximately 3 mm.

17. A method for quantifying and evaluating naturally occurring induced fluorescence in human skin, in vivo, comprising the steps of:
including an untreated subject area to endogenous fluorescence by application of laser energy;
sensing spectra of the induced endogenous fluorescent radiation;
obtaining a measure of intensity of said induced endogenous fluorescent radiation spectra over a predetermined frequency band; and
using said measure of intensity as a basis to make comparisons between different test subject areas for diagnostic purposes.

18. The method of claim 17, wherein said inducing step includes exposing said skin to laser energy having a wavelength of approximately 325 nm.

19. The method of claim 18, wherein said exposing step includes exposing said skin to laser energy at a level of from 1 to 10 mW at a distance of 0 to approximately 3 mm.

20. The method of claim 18, wherein said frequency band wavelength of said measure of intensity is from 350 to 750 nm.

21. The method of claim 17, wherein said using step includes the step of employing a pattern of measured intensities over an area of skin.

22. The method of claim 21, wherein said pattern recognition step includes forming a ratio of the measured intensity at two preselected wavelengths.

23. The method of claim 22, wherein said two wavelengths are approximately 390 nm and 429 nm.

24. The method of claim 22 including the step of employing said ratio to determine the degree of long term exposure of the skin to solar ultraviolet radiation.

25. The method of claim 24, wherein different test subject areas of said using step includes solar-exposed skin and non-solar exposed skin of the same subject.

26. The method of claim 17, wherein said subject area has a particular pigment, wherein said using step including using said measure of intensity to determine the degree of pigmentation of the subject area.

27. The method of claim 26, wherein the measure of intensity is inversely proportional to pigmentation.

28. The method of claim 17 wherein said method includes the step of evaluating changes in skin pigmentation by said measure of intensity.

29. A method for inducing naturally occurring fluorescence, in vivo, in human skin and for measuring and quantifying such induced fluorescence for diagnostic purposes comprising the steps of:
developing laser light energy having a predetermined wavelength and power;
directing said laser light energy to an untreated area of skin of an individual to induce endogenous fluorescence;
sending spectra of endogenous fluorescent radiation induced from said skin area;
obtaining a measure of intensity of said induced radiation spectra over a predetermined frequency band; and
using said measure of intensity as a basis to make comparisons for diagnostic purposes between said skin area and other skin areas of the same individual.

* * * * *

UNITED STATES PATENT AND TRADEMARK OFFICE
CERTIFICATE OF CORRECTION

PATENT NO. : 4,894,547
DATED : 1/16/90
INVENTOR(S) : David Leffell, Lawrence Deckelbaum It is certified that error appears in the above-identified patent and that said Letters Patent is hereby corrected as shown below:

Column 1, line 7, before " Background Of The Invention " insert :

The invention identified above is a subject invention under 35 U.S.C. 200, et seq., and the Standard Patent Rights Clause at 37 C.F.R. 401.14 or F.A.R. 52.227-11, which are included among the terms of the above-identified grant/contract award from the Public Health Service/National Institutes of Health.

Signed and Sealed this

Eleventh Day of May, 1999

Attest:

Q. TODD DICKINSON

Attesting Officer

Acting Commissioner of Patents and Trademarks